United States Patent
Lust

(10) Patent No.: US 8,848,191 B2
(45) Date of Patent: Sep. 30, 2014

(54) PHOTOACOUSTIC SENSOR WITH MIRROR

(75) Inventor: Lisa Lust, Minneapolis, MN (US)

(73) Assignee: Honeywell International Inc., Morristown, NJ (US)

( * ) Notice: Subject to any disclaimer, the term of this patent is extended or adjusted under 35 U.S.C. 154(b) by 379 days.

(21) Appl. No.: 13/419,827

(22) Filed: Mar. 14, 2012

(65) Prior Publication Data

US 2013/0239658 A1    Sep. 19, 2013

(51) Int. Cl.
*G01N 21/00*    (2006.01)

(52) U.S. Cl.
USPC .......................................................... 356/437

(58) Field of Classification Search
CPC ..................................................... G01N 21/00
USPC ......................................... 356/437–440, 442
See application file for complete search history.

(56) References Cited

U.S. PATENT DOCUMENTS

| | | | |
|---|---|---|---|
| 3,820,901 A * | 6/1974 | Kreuzer | 356/425 |
| 3,995,960 A * | 12/1976 | Fletcher et al. | 356/433 |
| 4,253,770 A | 3/1981 | Horiba | |
| 4,273,450 A | 6/1981 | Watanabe et al. | |
| 4,399,689 A | 8/1983 | Bechthold et al. | |
| 4,413,504 A | 11/1983 | Voigtman et al. | |
| 4,436,428 A | 3/1984 | Watanabe et al. | |
| 4,457,162 A | 7/1984 | Rush et al. | |
| 4,529,319 A | 7/1985 | Muller | |
| 4,533,252 A | 8/1985 | Cahen et al. | |
| 4,557,603 A | 12/1985 | Oehler et al. | |
| 4,622,845 A | 11/1986 | Ryan et al. | |
| 4,722,602 A | 2/1988 | Kitamori et al. | |
| 4,740,086 A | 4/1988 | Oehler et al. | |
| 4,866,681 A | 9/1989 | Fertig | |
| 5,028,864 A | 7/1991 | Lee et al. | |
| 5,085,080 A | 2/1992 | Yu | |
| 5,159,411 A | 10/1992 | Hammerich et al. | |
| 5,268,911 A | 12/1993 | Young | |
| 5,726,752 A * | 3/1998 | Uno et al. | 356/246 |
| 5,753,797 A | 5/1998 | Forster et al. | |
| 5,766,957 A * | 6/1998 | Robinson et al. | 436/165 |
| 5,841,017 A | 11/1998 | Baraket et al. | |
| 5,869,749 A | 2/1999 | Bonne et al. | |
| 5,900,533 A | 5/1999 | Chou | |
| 5,913,234 A | 6/1999 | Julliard et al. | |
| 5,933,245 A | 8/1999 | Wood et al. | |
| 6,006,585 A | 12/1999 | Forster | |
| 6,043,884 A | 3/2000 | Curbelo | |
| 6,070,093 A | 5/2000 | Oosta et al. | |
| 6,082,178 A | 7/2000 | Bernstein | |

(Continued)

FOREIGN PATENT DOCUMENTS

| DE | 3817791 A1 | 12/1989 |
|---|---|---|
| DE | 4018393 A1 | 12/1990 |

(Continued)

*Primary Examiner* — Roy M Punnoose
(74) *Attorney, Agent, or Firm* — Schwegman Lundberg & Woessner, P.A.

(57) ABSTRACT

A photoacoustic sensing device includes a laser tuned to emit light to cause optical absorption by a gas to be detected, a resonant acoustic sensor positioned to receive pressure waves from the gas, wherein the laser is modulated to match a resonant frequency of the resonant acoustic sensor, and a first mirror positioned to receive light from the laser after the light has passed through the gas and to reflect the received light back through the gas to cause additional optical absorption.

20 Claims, 2 Drawing Sheets

(56) References Cited

U.S. PATENT DOCUMENTS

| | | | |
|---|---|---|---|
| 6,108,096 | A | 8/2000 | Ushio et al. |
| 6,160,255 | A | 12/2000 | Sausa |
| 6,161,426 | A | 12/2000 | Byatt |
| 6,222,190 | B1 | 4/2001 | Bernstein |
| 6,236,455 | B1 | 5/2001 | Autrey et al. |
| 6,344,647 | B1 | 2/2002 | Jourdain et al. |
| 6,466,806 | B1 | 10/2002 | Geva et al. |
| 6,474,168 | B1 | 11/2002 | Meringdal |
| 6,552,792 | B1 | 4/2003 | Pilgrim et al. |
| 6,594,016 | B1 | 7/2003 | Te Lintel Hekkert |
| 6,608,683 | B1 | 8/2003 | Pilgrim et al. |
| 6,644,128 | B1 | 11/2003 | Byatt et al. |
| 6,694,173 | B1 | 2/2004 | Bende et al. |
| 7,034,943 | B1 | 4/2006 | Moeckli et al. |
| 7,213,444 | B2 | 5/2007 | Baraket et al. |
| 7,245,380 | B2 | 7/2007 | Kosterev |
| 7,263,871 | B2 | 9/2007 | Selker et al. |
| 7,288,775 | B2 | 10/2007 | Fujinoki et al. |
| 7,304,732 | B1 | 12/2007 | Polcawich et al. |
| 7,345,766 | B2 | 3/2008 | Schindler et al. |
| 7,595,463 | B2 | 9/2009 | Weick et al. |
| 7,605,922 | B2 | 10/2009 | Willing et al. |
| 7,663,756 | B2 | 2/2010 | Cole |
| 7,864,326 | B2 | 1/2011 | Cox et al. |
| 8,085,403 | B2 | 12/2011 | Fritz et al. |
| 8,339,607 | B2 * | 12/2012 | Levine et al. ............... 356/432 |
| 2002/0093648 | A1 | 7/2002 | Nikoonahad et al. |
| 2002/0093658 | A1 | 7/2002 | Han |
| 2002/0158202 | A1 | 10/2002 | Webber et al. |
| 2002/0194897 | A1 | 12/2002 | Arnott et al. |
| 2003/0038237 | A1 | 2/2003 | Webber |
| 2003/0080295 | A1 | 5/2003 | Webber et al. |
| 2003/0089170 | A1 | 5/2003 | Amonette et al. |
| 2003/0090663 | A1 | 5/2003 | Autrey et al. |
| 2003/0090664 | A1 | 5/2003 | Amonette et al. |
| 2003/0112019 | A1 | 6/2003 | Forster et al. |
| 2003/0184733 | A1 | 10/2003 | Kameoka et al. |
| 2003/0188581 | A1 | 10/2003 | Roudil et al. |
| 2003/0225320 | A1 | 12/2003 | Jeon et al. |
| 2004/0095579 | A1 | 5/2004 | Bisson et al. |
| 2004/0114130 | A1 | 6/2004 | Nguyen et al. |
| 2004/0127777 | A1 | 7/2004 | Ruchti et al. |
| 2004/0128081 | A1 | 7/2004 | Rabitz et al. |
| 2004/0179187 | A1 | 9/2004 | Mettes |
| 2004/0179200 | A1 | 9/2004 | Yoon et al. |
| 2005/0030539 | A1 | 2/2005 | Uber |
| 2005/0117155 | A1 | 6/2005 | Kosterev |
| 2005/0160791 | A1 | 7/2005 | Kung |
| 2006/0123884 | A1 | 6/2006 | Selker |
| 2006/0126070 | A1 | 6/2006 | Kauppinen |
| 2006/0138327 | A1 | 6/2006 | Kauppinen |
| 2006/0217626 | A1 | 9/2006 | Patel et al. |
| 2006/0256339 | A1 | 11/2006 | Lowney |
| 2007/0151325 | A1 | 7/2007 | Kauppinen |
| 2007/0206193 | A1 | 9/2007 | Pesach |
| 2007/0229834 | A1 | 10/2007 | Patel |
| 2008/0127715 | A1 | 6/2008 | Kosterev |
| 2009/0128819 | A1 | 5/2009 | Van Kesteren et al. |
| 2009/0174884 | A1 | 7/2009 | Kosterev |
| 2009/0229345 | A1 | 9/2009 | Van Kesteren |
| 2009/0288474 | A1 | 11/2009 | Kalkman |
| 2009/0303476 | A1 | 12/2009 | Kosterev et al. |
| 2010/0011836 | A1 | 1/2010 | Kalkman et al. |
| 2010/0014086 | A1 | 1/2010 | Cole |
| 2010/0033722 | A1 | 2/2010 | Van Neste et al. |
| 2010/0043526 | A1 | 2/2010 | Helwegen |
| 2010/0045990 | A1 | 2/2010 | Van Kesteren et al. |
| 2010/0045991 | A1 | 2/2010 | Miklos et al. |
| 2010/0045998 | A1 | 2/2010 | Fritz |
| 2010/0101305 | A1 | 4/2010 | Miklos et al. |
| 2010/0147051 | A1 | 6/2010 | Tobias |
| 2011/0201914 | A1 | 8/2011 | Wang et al. |
| 2012/0062896 | A1 * | 3/2012 | Familia et al. ............... 356/437 |

FOREIGN PATENT DOCUMENTS

| | | | |
|---|---|---|---|
| DE | 4116280 | A1 | 12/1991 |
| DE | 4411853 | A1 | 10/1995 |
| DE | 4446723 | A1 | 1/1996 |
| DE | 102005030151 | B3 | 11/2006 |
| DE | 102005053121 | A1 | 5/2007 |
| EP | 0369176 | A2 | 5/1990 |
| EP | 0590813 | A1 | 4/1994 |
| EP | 829225 | A2 | 3/1996 |
| EP | 829224 | A2 | 3/1998 |
| EP | 1386690 | A1 | 2/2004 |
| EP | 1564543 | A2 | 8/2005 |
| EP | 1574840 | A1 | 9/2005 |
| EP | 1574841 | A1 | 9/2005 |
| EP | 1582857 | A1 | 10/2005 |
| FR | 2791134 | A1 | 9/2000 |
| JP | 60-143743 | A | 7/1985 |
| JP | 60-195438 | A | 10/1985 |
| JP | 61-031930 | A | 2/1986 |
| JP | 1-155270 | A | 6/1989 |
| JP | 2002-174626 | A | 6/2002 |
| WO | WO-93/06457 | A1 | 4/1993 |
| WO | WO-96/02820 | A1 | 2/1996 |
| WO | WO-96/31765 | A1 | 10/1996 |
| WO | WO-02/23160 | A1 | 3/2002 |
| WO | WO-02/088697 | A1 | 11/2002 |
| WO | WO-02/088698 | A1 | 11/2002 |
| WO | WO-03/100393 | A1 | 12/2003 |
| WO | WO-2005/077061 | A2 | 8/2005 |
| WO | WO-2005/095949 | A1 | 10/2005 |
| WO | WO-2006/072867 | A1 | 7/2006 |
| WO | WO-2006/092751 | A1 | 9/2006 |
| WO | WO-2006/114766 | A2 | 11/2006 |
| WO | WO-2007/056772 | A2 | 5/2007 |
| WO | WO-2008/030250 | A2 | 3/2008 |

* cited by examiner

PHOTOACOUSTIC SENSOR WITH MIRROR

BACKGROUND

Photo-acoustic gas sensors operate by heating a gas using a laser tuned to a gas absorption line corresponding to a gas to be detected, such as hydrogen sulfide. If the gas is present even at part per million levels optical absorption occurs, which causes local heating and results in thermal expansion (pressure waves). The pressure waves are an acoustic signature that may be detected by a microphone or other acoustic pressure responsive sensor.

An alternative mechanism for measuring the presence of a specific gas includes a direct extinction method that measures light intensity before and after a gas absorption cell. Conclusions can be drawn regarding the concentration of the light-absorbing gas from the difference of the two measurements. This method permits analysis in flowing gas. However, it is only suitable for determination of relatively high gas concentrations, unless very considerable cell lengths or multiple reflection cells can be accepted. However, in the latter case it is necessary for the incident light beam to be narrowly focused and the mirror system must be very accurately adjusted. Multiple reflection cells used in such a mirror system are generally very complicated and costly. Environmental factors can adversely affect the performance of such mirror systems.

SUMMARY

A photoacoustic sensing device includes a laser tuned to emit light to cause optical absorption by a gas to be detected, a resonant acoustic sensor positioned to receive pressure waves from the gas, wherein the laser is modulated to match a resonant frequency of the resonant acoustic sensor, and a first mirror positioned to receive light from the laser after the light has passed through the gas and to reflect the received light back through the gas to cause additional optical absorption.

A method includes projecting a laser beam toward gas, wherein the laser beam is tuned to at least one gas absorption line of a gas to be detected, detecting pressure waves generated by optical absorption of the laser beam by the gas to be detected, and reflecting the laser beam back through the gas to increase an amplitude of the generated pressure waves.

DETAILED DESCRIPTION

In the following description, reference is made to the accompanying drawings that form a part hereof, and in which is shown by way of illustration specific embodiments which may be practiced. These embodiments are described in sufficient detail to enable those skilled in the art to practice the invention, and it is to be understood that other embodiments may be utilized and that structural, logical and electrical changes may be made without departing from the scope of the present invention. The following description of example embodiments is, therefore, not to be taken in a limited sense, and the scope of the present invention is defined by the appended claims.

Figure 1:
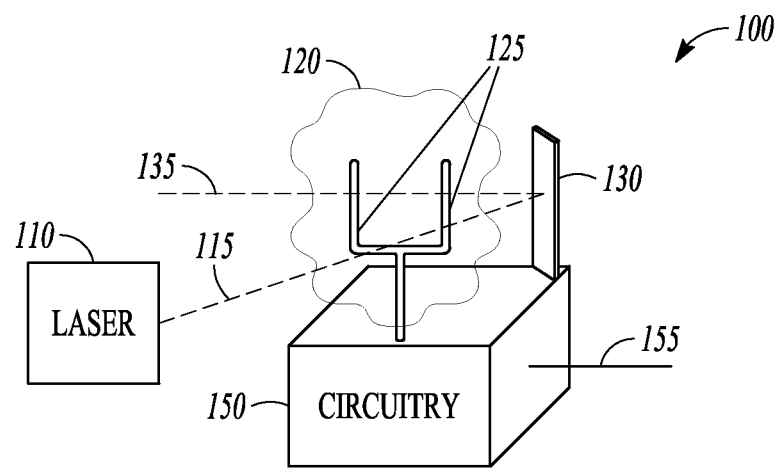
FIG. 1 is a block schematic diagram of a photoacoustic sensing device having a mirror according to an example embodiment.

A photoacoustic sensing device is illustrated generally at 100 in schematic form in FIG. 1 according to an example embodiment. The sensing device 100 includes a laser 110 tuned to emit light 115 to cause optical absorption by a gas of interest in a gas 120. A resonant acoustic sensor, such as a microphone or a tuning fork 125 is positioned to receive pressure waves from the gas. In one embodiment, the laser emits light 115 in the form of a beam that is modulated to match a resonant frequency of the tuning fork.

In one embodiment, the tuning fork 125 is a microelectromechanical systems (MEMS) resonant quartz tuning fork (QTF). The laser light is modulated at the QTF resonant frequency. The laser light 115 and gas 120 are positioned proximate the tuning fork 125 tines to optimize receipt of pressure waves from the optically heated gas. In one embodiment, the tuning fork is positioned within the gas, and the light is projected between the tines of the tuning fork. In further embodiments, the gas and light may be adjacent the tuning fork, yet sufficiently proximate the tuning fork such that pressure waves created by absorption of radiation by a gas of interest are received by the tuning fork to cause motion of the tuning fork. When the laser passes in front of the tuning fork, such an arrangement may be referred to as off axis.

A first mirror 130 is positioned to receive light 115 from the laser 110 after the light has passed through the gas 125 and to reflect the received light as indicated at 135 back through the gas 125 to cause additional optical absorption. The reflected light effectively increases the overall laser power available to heat the localized gas and increase the pressure waves created without adding additional noise. The first mirror 130 may be positioned to reflect the light back at an angle from the first light to ensure the light is not reflected back at the laser 110. By reflecting the light back through the gas, the signal to noise ratio is enhanced. The enhanced signal to noise ratio allows the use of lower power lasers such as low cost VCSELs, driving the cost of manufacture of a sensor lower. The mirrors need not be precisely aligned, since it is only desired that the light pass through the gas a desired number of times. The light also does not need to be in resonance with the mirror cavity mode, such as in a ring down cavity.

In one embodiment, the tuning fork is supported by a circuit board 150 that may contain circuitry to convert a small current generated by movement of the tuning fork into a voltage, such as by use of a transimpedance amplifier. The voltage may be converted to a digital signal by an analog to digital converter for processing and providing an output 155 representative of the concentration of the gas of interest in gas 120. The substrate 130 may also be used to support the mirror 130. In further embodiments, a separate substrate may be used to support the laser, sensor, mirror, and circuitry is proper relation to each other.

The mirror may formed by using silicon wafers with a reflective coating. In one embodiment, a mirror which possess 99% reflectance in the wavelength band of the desired gas absorption line may be used. This would enable significant signal enhancement over the use of a single beam of light. Many toxic gas species such as hydrogen sulfide have reduced absorption cross section. The increased signal to noise ratio facilitates ever lower concentrations to be detected.

Figure 2:
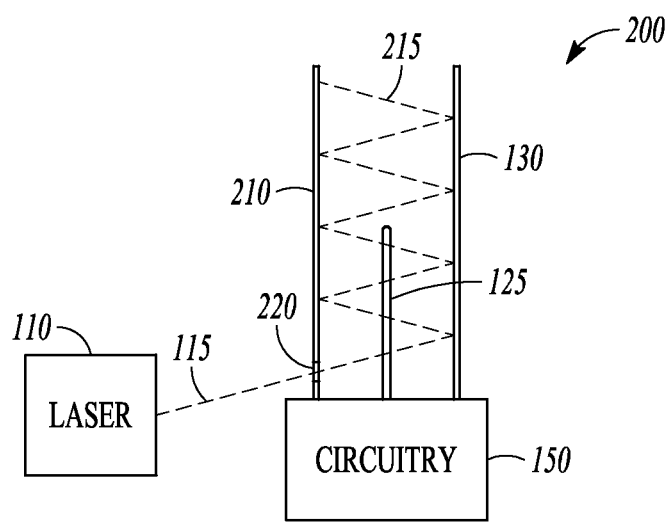
FIG. 2 is a block schematic diagram of a photoacoustic sensing device having multiple mirrors according to an example embodiment.

FIG. 2 is a schematic block diagram of an alternative embodiment generally at 200. Utilizing reference numbers for like parts from FIG. 1, a laser 110 is positioned to project a laser beam 115 toward a gas proximate a sensor 125. The beam 115 is reflected by first mirror 130 toward a second mirror 210 positioned relative to the first mirror to cause multiple further reflections of light through the gas between the first and second mirrors as illustrated by broken line 215. In one embodiment, the first and second mirrors are positioned outside a range that would create a resonant cavity for the laser light.

In one embodiment, the second mirror 210 is positioned between the laser 110 and the first mirror 130 and contains an opening 220 to allow laser light to pass through the second mirror 210 to reach the first mirror 130. The reflections are angled slightly from orthogonal to gradually traverse a length of the mirrors before ending.

In one embodiment, the laser is positioned to project light onto the first mirror at an angle from orthogonal to facilitate reflection back toward the second mirror at a suitable physical displacement from the opening. The first and second mirrors are substantially parallel to each other to reflect the laser light multiple times over a length of the mirrors. In one embodiment, each reflection of the light by a mirror results in approximately 99% of the light being reflected. After fifty or so reflections, the power level remaining in the beam is fairly low, and further reflections would provide little additional benefit. The absorption cross section of the gas of interest is generally much smaller than the attenuation caused by the reflections, and may essentially be ignored for determining a desired number of reflections.

In one embodiment, the tuning fork is positioned between the two mirrors to receive the pressure waves and not receive the laser light. The laser light and gas may be positioned proximate the tuning fork to optimize receipt of pressure waves from the optically heated gas. The two mirrors may create a cavity to facilitate travel of the pressure waves to the tuning fork in some embodiments. It should be noted that given the speed of the beam compared to the rate of expansion of the gas caused by the beam, the multiple reflections occur quickly enough to not adversely affect the generation of the pressure waves by attenuation of the beam to correspond to the resonant frequency of the tuning fork.

The tuning fork may be a microelectricalmechanical systems (MEMS) tuning fork in some embodiments. One example tuning fork includes an R38 Raltron tuning fork. Other tuning forks or different types of acoustic pressure sensors may be used in further embodiments.

The mirrors, as above, may be formed by using silicon wafers with a reflective coating. In one embodiment, a mirror which possesses 99% reflectance in the wavelength band of the desired gas absorption line may be used. This would enable about a 40 times signal enhancement over the use of a single beam of light. The wafers may be bonded together with streets of photoresistive spacers. The cavity being formed in one embodiment is not a resonant cavity. As the cavity is a reflective non-resonant cavity, spacing of the mirrors need not be precise. The mirror positioning is thus robust against temperature and vibration environmental factors since the overall mirror spacing is not critical to maintain. In one embodiment, the mirrors may be positioned substantially parallel to each other to ensure a desired number of reflections of the beam.

The opening 220 in the second mirror may be a 100 micron entrance hole formed such as by etching or drilling to enable the light to enter the cavity. Other size openings may be used in further embodiments, and the size may depend on the beam width of the laser, which can vary for different size and cost laser sources.

Figure 3:
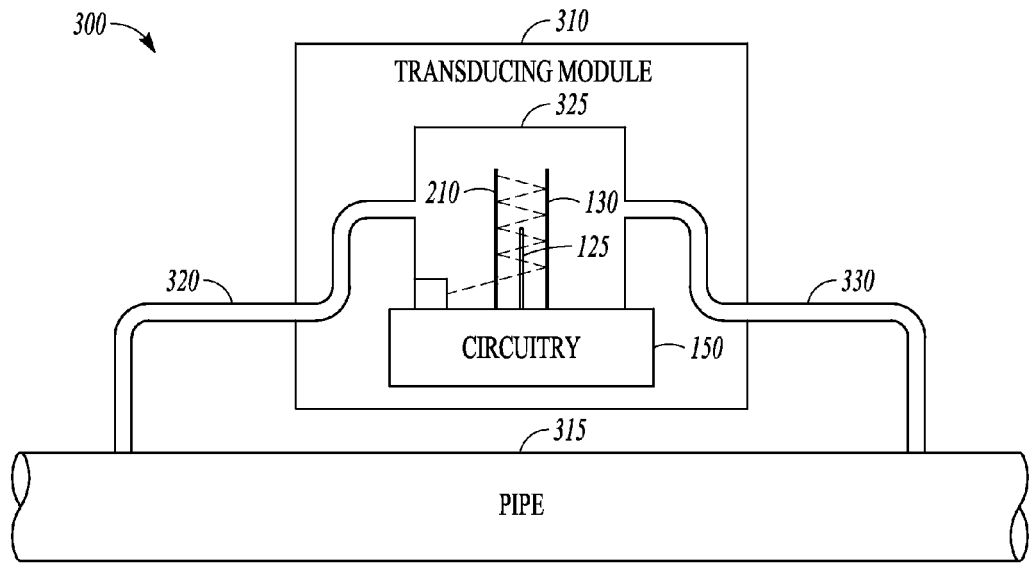
FIG. 3 is a block schematic diagram of a photoacoustic sensing device coupled to a gas line according to an example embodiment.

FIG. 3 is a block schematic diagram of an acoustic sensing device indicated generally at 300. A transducing module 310 is shown coupled to a gas supply such as a pipe 315. In one embodiment, a supply line 320 is coupled to the pipe 315 to deliver a sample of gas to the module 310. In one embodiment, module 310 corresponds to device 200 from FIG. 2. A two mirror cavity is used to reflect a laser beam through a gas sample multiple times. The device 200 is enclosed in a cavity 325 that contains gas supplied by line 320. Line 320 may have valves if desired to sample the gas at discrete intervals in one embodiment, or may simply provide a gas to the cavity 325 at a rate sufficient to allow detection. A return pipe 330 may return sampled gas to the pipe 315 in further embodiments. In still further embodiments, the gas may simply be sampled from a surrounding environment. The transducer may be exposed to ambient as indicated in FIG. 2, or may be enclosed within a cavity 325 as illustrated in FIG. 3, with ambient gas being provided by line 320.

In further embodiments, an acoustic sensing device, such as device 100 or 200 may be used to sample ambient environmental conditions, and need not utilize pipes or pumps to provide the gas to be measured. While a small pump might be used to pull in surrounding gas, the gas may instead be allowed to diffuse proximate the sensing device without the use of a pump or gas line.

Figure 4:
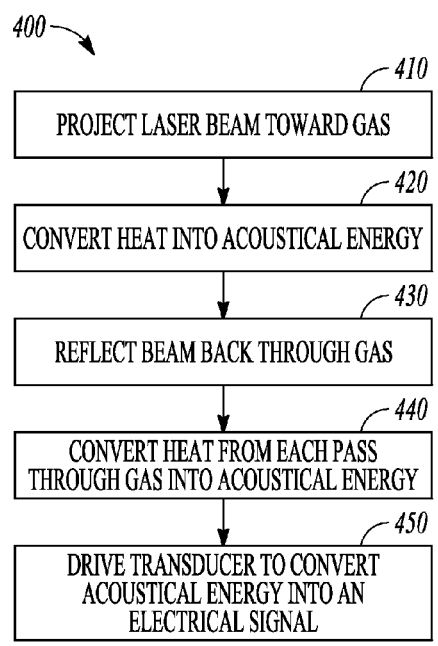
FIG. 4 is a block flow diagram illustrating a method of photoacoustic sensing of gas according to an example embodiment.

An example method is illustrated at 400 in FIG. 4, and includes projecting a laser beam toward gas at 410 that may contains molecules to be detected. The laser in one embodiment is modulated at a resonant frequency of an acoustic resonant transducer. The laser beam may be tuned to at least one gas absorption line of the gas molecules to be detected. The laser beam radiation is absorbed by the desired molecules and converted into acoustical energy at 420. Reflecting the laser beam back through the gas is done at 430 to increase an amplitude of the generated pressure waves at 440. The resulting modulated acoustical wave or pressure waves drive the transducer at 450. The transducer converts the acoustic energy into an electrical signal. The gas absorbs more laser radiation each time the beam is reflected back and forth in a non-resonant mirror cavity, effectively increasing signal strength without adding noise.

In one embodiment, the laser is modulated at a resonant frequency of a pressure wave detector. The pressure waves are detected by a tuning fork. The electrical signal may be processed to indicate whether or not the gas to be detected is present.

Example Embodiments

1. A photoacoustic sensing device comprising:
   a laser tuned to emit light to cause optical absorption by a gas to be detected;
   a resonant sensor positioned to receive pressure waves from the gas, wherein the laser is modulated to match a resonant frequency of the resonant sensor; and
   a first mirror positioned to receive light from the laser after the light has passed through the gas and to reflect the received light back through the gas to cause additional optical absorption.

2. The device of example 1 and further comprising a second mirror positioned relative to the first mirror to cause multiple further reflections of light through the gas between the first and second mirrors.

3. The device of example 2 wherein the first and second mirror are positioned outside a range that would create a resonant cavity for the laser light.

4. The device of example 2 or 3 wherein the second mirror is positioned between the laser and the first mirror and contains an opening to allow laser light to pass through the second mirror to reach the first mirror.

5. The device of example 2, 3, or 4 wherein the laser is positioned to project light onto the first mirror at an angle from orthogonal to facilitate reflection back toward the second mirror at a suitable physical displacement from the opening.

6. The device of example 2, 3, 4, or 5 wherein the first and second mirrors are substantially parallel to each other to reflect the laser light multiple times over a length of the mirrors.

7. The device of example 2, 3, 4, 5, or 6 wherein the resonant sensor comprises a tuning fork that is positioned between the two mirrors to receive the pressure waves and not receive the laser light.

8. The device of example 2, 3, 4, 5, 6, or 7 wherein the resonant sensor is a microelectricalmechanical systems (MEMS) tuning fork.

9. The device of any one of examples 1-8 wherein the laser light and gas are positioned proximate the tuning fork to optimize receipt of pressure waves from the optically heated gas.

10. A method comprising:
projecting a laser beam toward gas, wherein the laser beam is tuned to at least one gas absorption line of a gas to be detected;
detecting pressure waves generated by optical absorption of the laser beam by the gas to be detected; and
reflecting the laser beam back through the gas to increase an amplitude of the generated pressure waves.

11. The method of example 10 and further comprising modulating the laser at a resonant frequency of a pressure wave detector.

12. The method of example 10 or 11 wherein the pressure waves are detected by a tuning fork.

13. The method of example 10, 11, or 12 and further comprising converting the pressure waves to an electrical signal.

14. The method of example 13 and further comprising processing the electrical signal to indicate whether or not the gas to be detected is present.

15. A method comprising:
positioning a pressure wave detector proximate a gas to be detected;
aiming a laser toward the gas to be detected, wherein the laser is tuned to a optical absorption line corresponding to a desired gas; and
positioning a first mirror to receive a laser beam that has gone through the gas to be detected such that it reflects the laser beam back through the gas to be detected.

16. The method of example 15 and further comprising positioning a second mirror to reflect the laser beam reflected by the first mirror back through the gas to be detected.

17. The method of example 16 and further comprising positioning the second mirror such that the laser beam is reflected back and forth between the first and second mirror through the gas to be detected several times.

18. The method of example 17 wherein the number of reflections is at least fifty.

19. The method of example 15, 16, 17, or 18 wherein the pressure detector comprises a piezoelectric tuning fork.

20. The method of example 19 wherein the first and second mirrors form a cavity that directs pressure waves from the gas to the piezoelectric tuning fork.

Although a few embodiments have been described in detail above, other modifications are possible. For example, the logic flows depicted in the figures do not require the particular order shown, or sequential order, to achieve desirable results. Other steps may be provided, or steps may be eliminated, from the described flows, and other components may be added to, or removed from, the described systems. Other embodiments may be within the scope of the following claims.

The invention claimed is:

1. A photoacoustic sensing device comprising:
a laser tuned to emit light to cause optical absorption by a gas to be detected;
a resonant sensor positioned to receive pressure waves from the gas, wherein the laser is modulated to match a resonant frequency of the resonant sensor; and
a first mirror positioned to receive light from the laser after the light has passed through the gas and to reflect the received light back through the gas to cause additional optical absorption.

2. The device of claim 1 and further comprising a second mirror positioned relative to the first mirror to cause multiple further reflections of light through the gas between the first and second mirrors.

3. The device of claim 2 wherein the first and second mirror are positioned outside a range that would create a resonant cavity for the laser light.

4. The device of claim 2 wherein the second mirror is positioned between the laser and the first mirror and contains an opening to allow laser light to pass through the second mirror to reach the first mirror.

5. The device of claim 4 wherein the laser is positioned to project light onto the first mirror at an angle from orthogonal to facilitate reflection back toward the second mirror at a suitable physical displacement from the opening.

6. The device of claim 5 wherein the first and second mirrors are substantially parallel to each other to reflect the laser light multiple times over a length of the mirrors.

7. The device of claim 6 wherein the resonant sensor comprises a tuning fork that is positioned between the two mirrors to receive the pressure waves and not receive the laser light.

8. The device of claim 2 wherein the resonant sensor is a microelectricalmechanical systems (MEMS) tuning fork.

9. The device of claim 1 wherein the laser light and gas are positioned proximate the tuning fork to optimize receipt of pressure waves from the optically heated gas.

10. A method comprising:
projecting a laser beam toward gas, wherein the laser beam is tuned to at least one gas absorption line of a gas to be detected;
detecting pressure waves generated by optical absorption of the laser beam by the gas to be detected; and
reflecting the laser beam back through the gas to increase an amplitude of the generated pressure waves.

11. The method of claim 10 and further comprising modulating the laser at a resonant frequency of a pressure wave detector.

12. The method of claim 11 wherein the pressure waves are detected by a tuning fork.

13. The method of claim 12 and further comprising converting the pressure waves to an electrical signal.

14. The method of claim 13 and further comprising processing the electrical signal to indicate whether or not the gas to be detected is present.

15. A method comprising:
  positioning a pressure wave detector proximate a gas to be detected;
  aiming a laser toward the gas to be detected, wherein the laser is tuned to a optical absorption line corresponding to a desired gas; and
  positioning a first mirror to receive a laser beam that has gone through the gas to be detected such that it reflects the laser beam back through the gas to be detected.

16. The method of claim 15 and further comprising positioning a second mirror to reflect the laser beam reflected by the first mirror back through the gas to be detected.

17. The method of claim 16 and further comprising positioning the second mirror such that the laser beam is reflected back and forth between the first and second mirror through the gas to be detected several times.

18. The method of claim 17 wherein the number of reflections is at least fifty.

19. The method of claim 15 wherein the pressure detector comprises a piezoelectric tuning fork.

20. The method of claim 19 wherein the first and second mirrors form a cavity that directs pressure waves from the gas to the piezoelectric tuning fork.

* * * * *